(12) United States Patent
Eskridge et al.

(10) Patent No.: US 8,545,530 B2
(45) Date of Patent: Oct. 1, 2013

(54) IMPLANTABLE ANEURYSM CLOSURE SYSTEMS AND METHODS

(75) Inventors: Joseph Eskridge, Clyde Hill, WA (US); Gilbert Clarke, Seattle, WA (US)

(73) Assignee: Pulsar Vascular, Inc., San Jose, CA (US)

( * ) Notice: Subject to any disclaimer, the term of this patent is extended or adjusted under 35 U.S.C. 154(b) by 1077 days.

(21) Appl. No.: 11/324,827

(22) Filed: Jan. 3, 2006

(65) Prior Publication Data
US 2007/0088387 A1 Apr. 19, 2007

Related U.S. Application Data

(60) Provisional application No. 60/728,052, filed on Oct. 19, 2005.

(51) Int. Cl.
*A61M 29/00* (2006.01)

(52) U.S. Cl.
USPC ........... 606/191; 606/200; 606/213; 623/1.11

(58) Field of Classification Search
USPC ................ 606/191, 200, 213; 623/1.11
See application file for complete search history.

(56) References Cited

U.S. PATENT DOCUMENTS

| | | |
|---|---|---|
| 3,868,956 A | 3/1975 | Alfidi et al. |
| 4,164,045 A | 8/1979 | Bokros et al. |
| 4,248,234 A | 2/1981 | Assenza et al. |
| 4,645,495 A | 2/1987 | Vaillancourt |
| 4,651,751 A | 3/1987 | Swendson et al. |
| 4,665,906 A | 5/1987 | Jervis |
| 4,706,671 A | 11/1987 | Weinrib |
| 4,710,192 A | 12/1987 | Liotta et al. |
| 4,739,768 A | 4/1988 | Engelson |
| 4,820,298 A | 4/1989 | Leveen et al. |
| 4,909,787 A | 3/1990 | Danforth |
| 4,994,069 A | 2/1991 | Ritchart et al. |
| 5,011,488 A | 4/1991 | Ginsburg |
| 5,074,869 A | 12/1991 | Daicoff |
| 5,122,136 A | 6/1992 | Guglielmi et al. |
| 5,226,911 A | 7/1993 | Chee et al. |

(Continued)

FOREIGN PATENT DOCUMENTS

| | | |
|---|---|---|
| CN | 1399530 A | 2/2003 |
| EP | 0820726 A2 | 1/1998 |

(Continued)

OTHER PUBLICATIONS

Micrus Corp.; "Concourse 14 Microcatheter" Product Brochure; Sunnyvale, CA, USA.

(Continued)

*Primary Examiner* — Gary Jackson
*Assistant Examiner* — Diane Yabut
(74) *Attorney, Agent, or Firm* — Perkins Coie LLP

(57) ABSTRACT

An implantable closure structure is delivered using minimally invasive techniques and inhibits the migration of liquid and particulate matter from inside a physiological cavity or opening, such as an aneurysm, as well as inhibiting the flow of liquid and particulate matter, such as from an associated blood vessel, into a physiological cavity or opening. The device has a flexible patch supported by a framework structure that covers the neck or opening of a cavity such as an aneurysm and may have anchoring structures for supporting the flexible patch in place across the opening.

17 Claims, 6 Drawing Sheets

(56) References Cited

U.S. PATENT DOCUMENTS

| | | |
|---|---|---|
| 5,250,071 A | 10/1993 | Palermo |
| 5,261,916 A | 11/1993 | Engelson |
| 5,263,964 A | 11/1993 | Purdy |
| 5,263,974 A | 11/1993 | Matsutani et al. |
| 5,271,414 A | 12/1993 | Partika et al. |
| 5,304,195 A | 4/1994 | Twyford, Jr. et al. |
| 5,334,168 A | 8/1994 | Hemmer |
| 5,342,386 A | 8/1994 | Trotta |
| 5,350,397 A | 9/1994 | Palermo et al. |
| 5,354,295 A | 10/1994 | Guglielmi et al. |
| 5,527,338 A * | 6/1996 | Purdy ............ 606/200 |
| 5,531,685 A | 7/1996 | Hemmer et al. |
| 5,578,074 A | 11/1996 | Mirigian |
| 5,624,449 A | 4/1997 | Pham et al. |
| 5,643,254 A | 7/1997 | Scheldrup et al. |
| 5,665,106 A | 9/1997 | Hammerslag |
| 5,669,931 A | 9/1997 | Kupiecki et al. |
| 5,693,067 A | 12/1997 | Purdy |
| 5,733,294 A | 3/1998 | Forber et al. |
| 5,733,329 A | 3/1998 | Wallace et al. |
| 5,749,890 A | 5/1998 | Shaknovich |
| 5,749,894 A | 5/1998 | Engelson |
| 5,759,194 A | 6/1998 | Hammerslag |
| 5,766,192 A | 6/1998 | Zacca |
| 5,769,884 A | 6/1998 | Solovay |
| 5,797,953 A | 8/1998 | Tekulve |
| 5,814,062 A | 9/1998 | Sepetka et al. |
| 5,843,103 A | 12/1998 | Wulfman |
| D407,818 S | 4/1999 | Mariant et al. |
| 5,895,391 A | 4/1999 | Farnholtz |
| 5,895,410 A | 4/1999 | Forber et al. |
| 5,910,145 A | 6/1999 | Fischell et al. |
| 5,911,737 A | 6/1999 | Lee et al. |
| 5,916,235 A | 6/1999 | Guglielmi |
| 5,925,060 A | 7/1999 | Forber |
| 5,925,062 A | 7/1999 | Purdy |
| 5,925,683 A | 7/1999 | Park |
| 5,928,260 A | 7/1999 | Chin et al. |
| 5,935,114 A | 8/1999 | Jang et al. |
| 5,935,148 A | 8/1999 | Villar et al. |
| 5,951,599 A | 9/1999 | McCrory |
| 5,968,068 A | 10/1999 | Dehdashtian et al. |
| 5,980,514 A | 11/1999 | Kupiecki et al. |
| 5,984,944 A | 11/1999 | Forber |
| 6,007,544 A | 12/1999 | Kim |
| 6,013,055 A | 1/2000 | Bampos et al. |
| 6,022,341 A | 2/2000 | Lentz |
| 6,036,720 A * | 3/2000 | Abrams et al. ............ 606/213 |
| 6,063,070 A | 5/2000 | Eder |
| 6,063,104 A * | 5/2000 | Villar et al. ............ 606/213 |
| 6,071,263 A | 6/2000 | Kirkman |
| 6,077,291 A | 6/2000 | Das |
| 6,090,125 A | 7/2000 | Horton |
| 6,093,199 A | 7/2000 | Brown et al. |
| 6,096,021 A | 8/2000 | Helm et al. |
| 6,096,034 A | 8/2000 | Kupiecki et al. |
| 6,102,917 A | 8/2000 | Maitland et al. |
| 6,110,191 A | 8/2000 | Dehdashtian et al. |
| 6,117,157 A | 9/2000 | Tekulve |
| 6,139,564 A | 10/2000 | Teoh |
| 6,146,339 A | 11/2000 | Biagtan et al. |
| 6,152,944 A | 11/2000 | Holman et al. |
| 6,168,615 B1 | 1/2001 | Ken et al. |
| 6,168,622 B1 * | 1/2001 | Mazzocchi ............ 623/1.2 |
| 6,174,322 B1 | 1/2001 | Schneidt |
| 6,183,495 B1 | 2/2001 | Lenker et al. |
| 6,193,708 B1 | 2/2001 | Ken et al. |
| RE37,117 E | 3/2001 | Palermo |
| 6,221,066 B1 | 4/2001 | Ferrera et al. |
| 6,221,086 B1 | 4/2001 | Forber |
| 6,224,610 B1 | 5/2001 | Ferrera |
| 6,228,052 B1 | 5/2001 | Pohndorf |
| 6,293,960 B1 | 9/2001 | Ken |
| 6,296,622 B1 | 10/2001 | Kurz et al. |
| 6,309,367 B1 | 10/2001 | Boock |
| 6,325,807 B1 | 12/2001 | Que |
| 6,344,048 B1 | 2/2002 | Chin et al. |
| 6,375,668 B1 * | 4/2002 | Gifford et al. ............ 606/200 |
| 6,383,174 B1 | 5/2002 | Eder |
| 6,398,791 B1 | 6/2002 | Que et al. |
| 6,478,773 B1 | 11/2002 | Gandhi et al. |
| 6,491,711 B1 | 12/2002 | Durcan |
| 6,517,515 B1 | 2/2003 | Eidenschink |
| 6,530,935 B2 | 3/2003 | Wensel et al. |
| 6,533,905 B2 | 3/2003 | Johnson et al. |
| 6,554,794 B1 | 4/2003 | Mueller et al. |
| 6,589,256 B2 | 7/2003 | Forber |
| 6,613,074 B1 * | 9/2003 | Mitelberg et al. ............ 623/1.11 |
| 6,616,681 B2 | 9/2003 | Hanson et al. |
| 6,626,889 B1 | 9/2003 | Simpson et al. |
| 6,626,928 B1 | 9/2003 | Raymond et al. |
| 6,638,268 B2 | 10/2003 | Niazi |
| 6,652,556 B1 | 11/2003 | Vantassel et al. |
| 6,663,607 B2 | 12/2003 | Slaikeu et al. |
| 6,663,648 B1 | 12/2003 | Trotta |
| 6,669,795 B2 | 12/2003 | Johnson et al. |
| 6,672,338 B1 | 1/2004 | Esashi et al. |
| 6,679,836 B2 | 1/2004 | Couvillon, Jr. |
| 6,679,903 B2 | 1/2004 | Kurz |
| 6,689,141 B2 | 2/2004 | Ferrera et al. |
| 6,694,979 B2 | 2/2004 | Deem et al. |
| 6,723,112 B2 | 4/2004 | Ho et al. |
| 6,740,073 B1 | 5/2004 | Saville |
| 6,740,277 B2 | 5/2004 | Howell et al. |
| 6,746,468 B1 | 6/2004 | Sepetka et al. |
| 6,780,196 B2 | 8/2004 | Chin et al. |
| 6,790,218 B2 | 9/2004 | Jayaraman |
| 6,824,553 B1 | 11/2004 | Samson et al. |
| 6,835,185 B2 | 12/2004 | Ramzipoor et al. |
| 6,863,678 B2 | 3/2005 | Lee et al. |
| 6,911,037 B2 | 6/2005 | Gainor et al. |
| 6,936,055 B1 | 8/2005 | Ken et al. |
| 6,939,055 B2 | 9/2005 | Durrant et al. |
| 7,011,094 B2 | 3/2006 | Rapacki et al. |
| 7,033,387 B2 | 4/2006 | Zadno-Azizi et al. |
| 7,122,043 B2 | 10/2006 | Greenhalgh et al. |
| 7,147,659 B2 | 12/2006 | Jones |
| 7,156,871 B2 | 1/2007 | Jones et al. |
| 7,229,461 B2 | 6/2007 | Chin et al. |
| 7,232,461 B2 | 6/2007 | Ramer |
| 7,267,679 B2 | 9/2007 | McGuckin, Jr. et al. |
| 7,569,066 B2 * | 8/2009 | Gerberding et al. ............ 606/200 |
| 2002/0107534 A1 | 8/2002 | Schaefer et al. |
| 2003/0009177 A1 | 1/2003 | Middleman et al. |
| 2003/0139802 A1 | 7/2003 | Wulfman et al. |
| 2003/0171739 A1 | 9/2003 | Murphy et al. |
| 2003/0181922 A1 | 9/2003 | Alferness |
| 2003/0195385 A1 | 10/2003 | DeVore |
| 2003/0195553 A1 * | 10/2003 | Wallace et al. ............ 606/200 |
| 2003/0212412 A1 | 11/2003 | Dillard et al. |
| 2004/0019324 A1 | 1/2004 | Duchamp |
| 2004/0068314 A1 | 4/2004 | Jones et al. |
| 2004/0087998 A1 | 5/2004 | Lee et al. |
| 2004/0111112 A1 | 6/2004 | Hoffmann |
| 2004/0143254 A1 | 7/2004 | Vanney |
| 2004/0158185 A1 | 8/2004 | Moran et al. |
| 2004/0167602 A1 | 8/2004 | Fischell et al. |
| 2004/0186491 A1 | 9/2004 | Klint et al. |
| 2004/0193206 A1 | 9/2004 | Gerberding et al. |
| 2004/0193246 A1 | 9/2004 | Ferrera |
| 2004/0210248 A1 | 10/2004 | Gordon et al. |
| 2004/0210298 A1 | 10/2004 | Rabkin et al. |
| 2004/0260241 A1 | 12/2004 | Yamamoto et al. |
| 2005/0021023 A1 | 1/2005 | Guglielmi et al. |
| 2005/0025797 A1 | 2/2005 | Wang et al. |
| 2005/0033349 A1 | 2/2005 | Jones et al. |
| 2006/0030929 A1 | 2/2006 | Musbach |
| 2006/0052862 A1 | 3/2006 | Kanamaru et al. |
| 2006/0264905 A1 | 11/2006 | Eskridge et al. |
| 2006/0264907 A1 | 11/2006 | Eskridge et al. |
| 2007/0067015 A1 | 3/2007 | Jones et al. |
| 2007/0106311 A1 | 5/2007 | Wallace et al. |
| 2007/0191884 A1 | 8/2007 | Eskridge et al. |
| 2007/0270902 A1 | 11/2007 | Slazas et al. |

| | | | |
|---|---|---|---|
| 2008/0039930 A1 | 2/2008 | Jones et al. | |
| 2008/0147100 A1 | 6/2008 | Wallace | |
| 2008/0221600 A1 | 9/2008 | Dieck et al. | |

FOREIGN PATENT DOCUMENTS

| | | |
|---|---|---|
| EP | 1269935 A2 | 1/2003 |
| EP | 0996372 B1 | 9/2004 |
| WO | WO 97/24978 A1 | 7/1997 |
| WO | WO-9726939 A1 | 7/1997 |
| WO | WO-9731672 A1 | 9/1997 |
| WO | 9905977 A1 | 2/1999 |
| WO | 9907294 A1 | 2/1999 |
| WO | WO-9907294 A1 | 2/1999 |
| WO | WO 99/15225 A1 | 4/1999 |
| WO | WO-0013593 A1 | 3/2000 |
| WO | WO-0130266 A1 | 5/2001 |
| WO | WO 02/13899 A1 | 2/2002 |
| WO | WO 02/071977 A2 | 9/2002 |
| WO | WO 02/078777 A1 | 10/2002 |
| WO | WO 02/087690 A1 | 11/2002 |
| WO | WO 03/059176 A2 | 7/2003 |
| WO | WO 2004/026149 A1 | 4/2004 |
| WO | WO 2004/105599 A1 | 12/2004 |
| WO | WO 2005/082279 A1 | 9/2005 |

OTHER PUBLICATIONS

Cordis Neurovascular, Inc.; "Masstransit Microcather," Product Brochure; No. 153-8383-3; Miami Lakes, FL, USA (2003).
Cordis Neurovascular, Inc.; "Prowler Select Plus Microcatheter," Product Brochure; No. 154-9788-1; Miami Lakes, FL, USA (2003).
Cordis Neurovascular, Inc.; "Rapid Transit Microcatheter," Product Brochure; No. 152-7369-2; Miami Lakes, FL, USA (2002).
Cordis Neurovascular, Inc.; "Prowler Select LP Microcatheter," Product Brochure; No. 155-2285; Miami Lakes, FL, USA (2004).
Gupta et al. SMST-2003: Proc. Intl. Conf. Shape Memory Superelastic Technol.; Pacific Grove, CA; p. 639; 2003.
Eskridge et al.; U.S. Appl. No. 11/117,815 entitled "Implantable spiral coil medical devices and methods for using such devices," filed Apr. 29, 2005.
Gerberding et al.; U.S. Appl. No. 12/554,850 entitled "Systems and methods for supporting or occluding a physiological opening or cavity," filed Sep. 4, 2009.
Polytetraflouroethylene Implants, DermNet NZ, Nov. 11, 2005, http://dermetnz.org/polytetrafluoroethylene.html.
International Search Report, Prosecution for PCT/US2006040907, May 1, 2008, International Search Authority, Alexandria Virginia.
Extended International Search Report, Prosecution for PCT/US2006040907, Nov. 19, 2009, European Patent Office, Berlin, Germany.
Singapore Examination Report, Jul. 12, 2009, Intellectual Property Office of Singapore.
International Search Report and Written Opinion for International Application No. PCT/US2009/056133, Mail Date Oct. 26, 2009, 11 pages.

\* cited by examiner

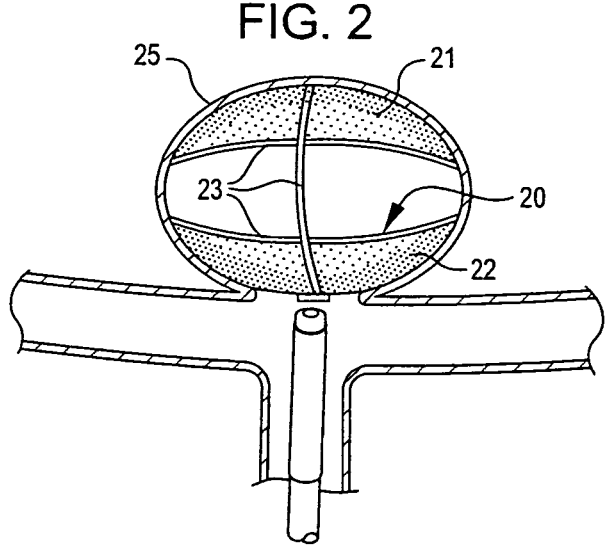
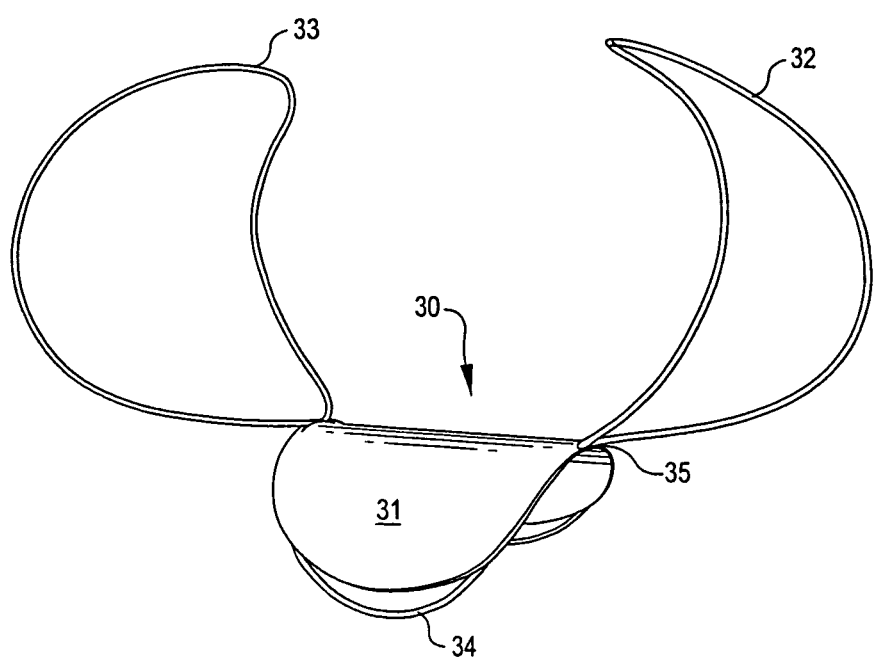

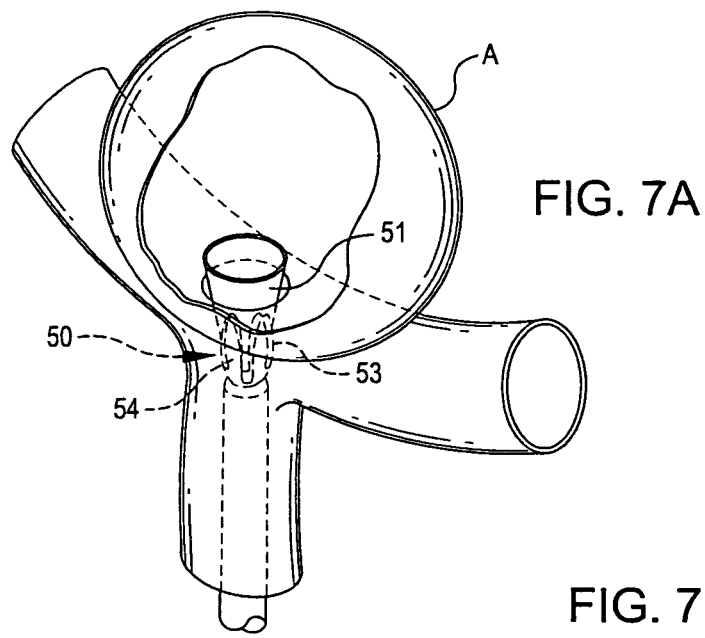
FIG. 7A
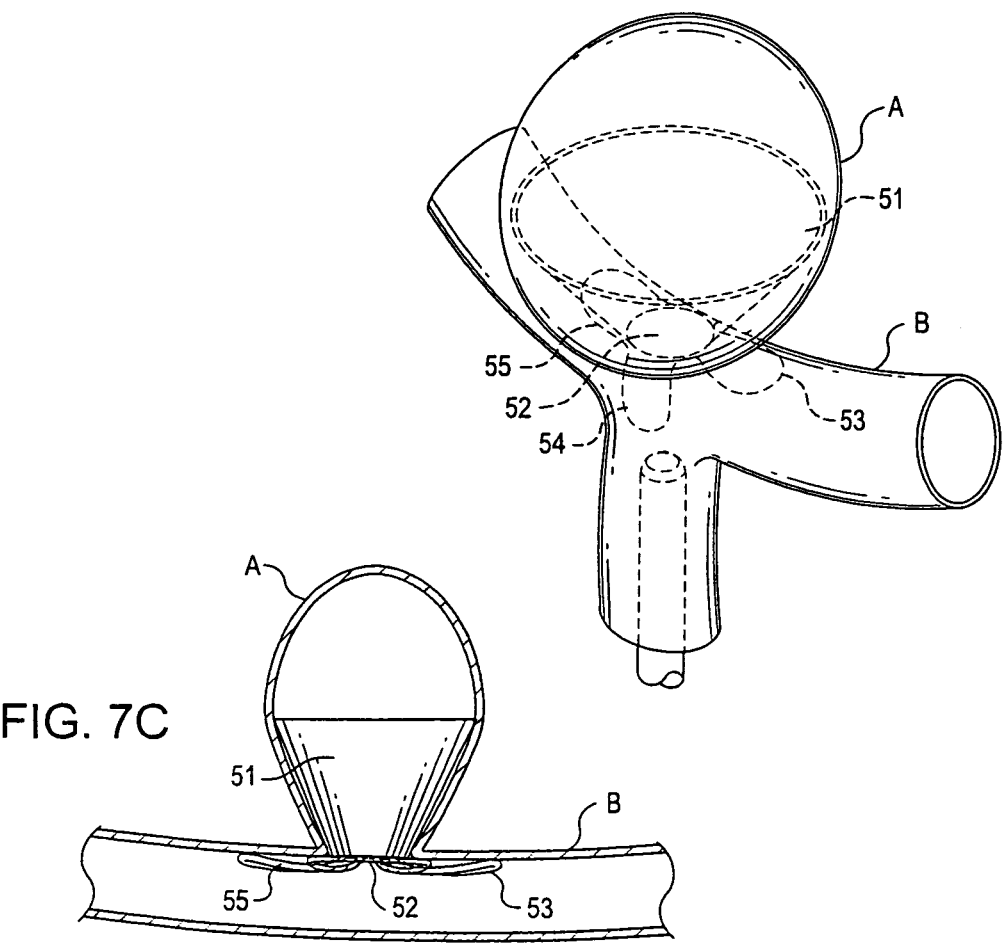
FIG. 7B
FIG. 7C

IMPLANTABLE ANEURYSM CLOSURE SYSTEMS AND METHODS

CROSS-REFERENCE TO RELATED APPLICATIONS

This application claims priority under 35 U.S.C. §119(e) to U.S. Provisional Patent Application No. 60/728,052 filed Oct. 19, 2005.

TECHNICAL FIELD OF THE INVENTION

The present invention relates generally to devices used in connection with minimally invasive treatments, such as treatments of defects in blood vessels or gas passageways of a mammal. More specifically, the invention relates to devices and systems for occluding aneurysms, other blood vessel irregularities and other passageway irregularities using minimally invasive techniques.

BACKGROUND OF THE INVENTION

Occlusive devices are placed within an opening or cavity in the body, such as in the vasculature, spinal column, fallopian tubes, bile ducts, bronchial and other air passageways and the like, and are generally delivered using minimally invasive surgical techniques. In general, an implantable device is guided to a desired site through a delivery catheter and may be pushed through an opening at the distal end of a delivery catheter by a pusher mechanism, such as a pusher or delivery wire, thereby deploying the device at the desired site. Once the occlusive device has been placed in the desired position, it is detached from the pusher mechanism without disturbing placement of the occlusive device or damaging surrounding structures.

Occlusive coils for implantation into anatomical defects such as aneurysms and other blood vessel abnormalities are well known. Aneurysms are bulges that form in an artery wall, generally caused by a weakening in the artery wall, that form an opening or cavity and are often the site of internal bleeding and stroke. In general, the minimally invasive therapeutic objective is to prevent material that collects or forms in the cavity from entering the bloodstream and to prevent blood from entering and collecting in the aneurysm. This is often accomplished by introducing various materials and devices into the aneurysm.

Various types of embolic agents and devices are used to reduce risks to a patient associated with the presence of an aneurysm. One class of embolic agents includes injectable fluids or suspensions, such as microfibrillar collagen, various polymeric beads, and polyvinylalcohol foam. These polymeric agents may be crosslinked (sometimes in vivo) to extend the persistence of the agent at the vascular site. These agents are often introduced into the vasculature through a catheter. After introduction and at the site, the introduced materials form a solid space-filling mass. Although some of these agents provide for excellent short term occlusion, many are thought to allow vessel recanalization due to absorption into the blood. Other materials, such as hog hair and suspensions of metal particles, have also been proposed and used to promote occlusions. Polymer resins, such as cyanoacrylates, are also employed as injectible vaso-occlusive materials. These resins are typically mixed with a radio-opaque contrast material or are made radio-opaque by the addition of a tantalum powder. Accurate and timely placement of these mixtures is crucial and very difficult. These materials are also difficult or impossible to retrieve once they have been placed in the vasculature.

Implantable vaso-occlusive metallic structures are also well known and commonly used. Many vaso-occlusive devices are provided in the configuration of helical coils and are constructed from a shape memory material that forms a desired coil configuration upon exiting the distal end of a delivery catheter. The purpose of the coil is to fill the space formed by a defect or injury and facilitate formation of an embolus with the associated allied tissue. Multiple coils of the same or different structure may be implanted serially in a single aneurysm or other vessel defect. Implantable framework structures are also used in an attempt to stabilize the wall of the aneurysm or defect prior to insertion of filling material such as coils.

Vaso-occlusive coils are generally constructed from metal or metal alloy wire forming a helical spiral. These devices may be formed from a shape change alloy and introduced to the target site through a catheter in a stretched linear form. The vaso-occlusive device assumes its predetermined, non-stretched three dimensional form upon discharge from the distal end of the catheter. Numerous coil and other three-dimensional structures are known in the art for occlusion of vascular abnormalities such as aneurysms.

Techniques for delivering a vaso-occlusive device to a target site generally involve a delivery catheter and a detachment mechanism that detaches the coil from a delivery mechanism after placement at the target site. A microcatheter is initially steered through the delivery catheter into or adjacent to the entrance of an aneurysm, typically aided by the use of a steerable guidewire. The guidewire is then withdrawn from the micro catheter lumen and replaced by the implantable vaso-occlusive coil. The vaso-occlusive coil is advanced through and out of the microcatheter and thus deposited within the aneurysm or other vessel abnormality. Implantation of the vaso-occlusive device within the internal volume of a cavity and maintenance of the device within the internal volume of the aneurysm is crucial. Migration or projection of a vaso-occlusive device from the cavity may interfere with blood flow or nearby physiological structures and poses a serious health risk.

One type of aneurysm, commonly known as a "wide neck aneurysm" is known to present particular difficulty in the placement and retention of vaso-occlusive coils. Wide neck aneurysms are generally referred to as aneurysms of vessel walls having a neck or an entrance zone from the adjacent vessel that is large compared to the diameter of the aneurysm or that is clinically observed to be too wide effectively to retain vaso-occlusive coils deployed using the techniques discussed above.

Devices for maintaining vaso-occlusive coils within an aneurysm have been proposed. One such device is described in U.S. Pat. No. 5,980,514, which discloses devices that are placed within the lumen of a feed vessel exterior to the aneurysm to retain coils within the aneurysm cavity. The device is held in place by means of radial pressure of the vessel wall. After the device is released and set in an appropriate place, a microcatheter is inserted into the lumen behind the retainer device and the distal end of the catheter is inserted into the aneurysm cavity for placement of one or more vaso-occlusive devices. The retainer device prevents migration of occlusion devices from the cavity.

Another methodology for closing an aneurysm is described in U.S. Pat. No. 5,749,894, in which a vaso-occlusive device such as a coil or braid has on its outer surface a polymeric composition that reforms or solidifies in situ to provide a barrier. The polymer may be activated, e.g. by the application of light, to melt or otherwise to reform the polymer exterior to the vaso-occlusive device. The vaso-occlusive device then sticks to itself at its various sites of contact and forms a rigid whole mass within the aneurysm.

Devices for bridging the neck of an aneurysm have been proposed. U.S. Patent Application 2003/0171739 A1, for example, discloses a neck bridge having one or more array elements attached to a junction region and a cover attached to the junction region and/or the array elements. The array elements may comprise Nitinol loops and the cover may comprise a fabric, mesh or other sheeting structure.

The placement of coils or other structures or materials in the internal space of an aneurysm or other defect hasn't been entirely successful. The placement procedure may be arduous and lengthy, requiring the placement of multiple coils serially in the internal space of the aneurysm. Debris and occlusive material may escape from within the aneurysm and present a risk of stroke, vessel blockage or other undesirable complications. Blood flows into aneurysm and other blood vessel irregularities after the placement of embolic devices, which increases the risks of complication. Furthermore, some aneurysms, vessels and other passageway defects aren't well-suited to placement of coils or other conventional occlusive devices. Wide neck aneurysms continue to present challenges in the placement and retention of vaso-occlusive coils.

Vaso-occlusive coils may be classified based upon their delivery mechanisms as pushable coils, mechanically detachable coils, and electrolytically detachable coils. Pushable coils are commonly provided in a cartridge and are pushed or "plunged" from the cartridge into a delivery catheter lumen. A pusher advances the pushable coil through and out of the delivery catheter lumen and into the site for occlusion. Mechanically detachable vasoocclusive devices are typically integrated with a pusher rod and are mechanically detached from the distal end of that pusher after exiting a delivery catheter. Electrolytically detachable vaso-occlusive devices are generally attached to a pusher by means of an electrolytically severable joint. The electrolytic joint may be severed by the placement of an appropriate voltage on the core wire. The joint erodes in preference either to the vaso-occlusive device itself or to the pusher core wire. The core wire is often simply insulated to prevent the electrolytic response caused by the imposition of electrical current.

Systems currently known, more generally, for the detachment of implantable devices after placement include mechanical systems, electrolytic systems and hydraulic systems. In mechanical systems, the occlusive device and the pusher wire are linked by means of a mechanical joint, or inter-locking linkage, which separates once the device exits the delivery catheter, thereby releasing the device. Examples of such systems include those taught in U.S. Pat. Nos. 5,263,964, 5,304,195, 5,350,397, and 5,261,916.

In electrolytic systems, a constructed joint (generally either fiber- or glue-based) connects the pusher wire to the occlusive device. Once the device has been placed in the desired position, the joint is electrolytically disintegrated by the application of a current or heat (for example, using a laser) by the physician. An example of such a system is provided in U.S. Pat. No. 5,624,449. Such systems have the disadvantage that dissolved material or gases generated by electrolysis may be released into the vasculature, thus presenting a potential hazard to the patient. Electrolytic detachment may also take more time to accomplish than is desirable during an interventional operation in which several occlusive devices are placed.

In hydraulic systems, the pushing wire is connected to the occlusive device by means of a polymer coupling. The pushing wire contains a micro-lumen to which the physician attaches a hydraulic syringe at the proximal end of the pusher wire. Upon the application of pressure on the syringe plunger, the hydraulic pressure increases and forces the polymer joint to swell and break, thereby releasing the device. An example of a hydraulic system is that described in U.S. Pat. No. 6,689,141.

U.S. Pat. No. 5,911,737 discloses a mechanism for releasing an implantable device that utilizes shape memory polymer microtubing that is heated above its phase transformation temperature, then shaped to hold a portion of the device to be implanted, and then cooled so that the device is retained by the tubing. Once the device has been positioned in the desired location, the microtubing is heated above its phase transformation temperature, thereby releasing the device.

Shape memory material is material that exhibits mechanical memory when activated by heat. Shape memory alloys have a transition temperature that depends upon the particular ratio of the metals in the alloy. Such alloys can be formed into a first shape when heated to a temperature sufficient for the material to reach its austenitic phase, and then plastically deformed into a second shape upon being brought below the transition temperature (martensitic state). When the alloy is reheated above its transition temperature, the alloy transforms from its martensitic phase to its austenitic phase and returns to its first, pre-set, shape. Shape memory alloys have been employed in implantable devices, as described, for example, in U.S. Pat. No. 3,868,956.

U.S. Pat. No. 5,578,074 discloses an implant delivery system which includes a pusher having a coupling portion formed of shape memory material which exhibits different configurations depending on the temperature. The coupling portion interlockingly engages the implant when it is in a generally bent or coiled configuration and releases the implant when thermally activated to assume its pre-set configuration. US Published Patent Application No. 2003/0009177 describes apparatus for manipulating matter, such as an implantable device within a body lumen, comprising a manipulator means constructed of one or more bent or twisted shape memory alloy (SMA) members having pseudoelasticity at body temperature, and a hollow housing capable of holding the SMA member in a relatively straightened state. On being extended from the housing at body temperature, the shape memory alloy member bends or twists in a lateral or helical direction in order to manipulate the device. On being withdrawn into the housing, the shape memory alloy member becomes relatively straightened.

Despite the variety of detachment mechanisms available, there is a continuing need for reliable, fast-acting mechanisms for detaching implantable devices that do not release material upon detachment and do not interfere with device placement or the surrounding physiological structures. The detachment mechanisms described herein are directed to meeting this need.

SUMMARY OF THE INVENTION

The present invention provides systems and methods for occluding an opening in an internal lumen or cavity within a subject's body using minimally invasive techniques. In general, these systems and methods are used in connection with vascular abnormalities or cavities and are described herein with reference to their application as aneurysm closure devices. It will be appreciated, however, that systems and methods of the present invention are not limited to these applications and may be implemented in a variety of medical indications in which isolation of a cavity or lumen or air passageway or the like is desired.

An intravascular guide catheter is generally inserted into a patient's vasculature, such as through the femoral artery, and guided through the vasculature to a desired site of intervention to repair, or treat, vascular abnormalities such as aneurysms. Implantable devices, accessories, drugs, and the like may be delivered to the site of intervention through the guide catheter. Additional delivery mechanisms and specialized catheters, such as microcatheters, pusher devices, and the like, may be used to facilitate delivery of various devices and accessories. Implantable devices are generally detachably mounted at the distal end of a catheter or a pusher or delivery mechanism and navigated through the guide catheter to the target site, where they are detached from the delivery mechanism. The delivery mechanism is then withdrawn through the guide catheter and additional devices, accessories, drugs or the like may be delivered to the target site.

The implantable devices of the present invention are particularly suitable as aneurysm closure devices for closing narrow- and wide-necked aneurysms as well as aneurysms located at or near a vessel bifurcation. The systems of the present invention inhibit the migration of liquid and particulate matter from the aneurysm to the vascular system and inhibit blood flow from the vasculature into the cavity formed by the aneurysm. Detachment systems and mechanisms for delivering implantable devices of the present invention are well known in the art.

In one embodiment, the implantable device of the present invention comprises a closure structure having a flexible patch supported in the proximity of its perimeter by a wire loop or framework structure. The closure structure is adjustable between a delivery condition in which it can be delivered in a smaller dimension configuration through a catheter system to a target site and a larger dimension, deployed configuration. The size and configuration of the flexible patch in the deployed condition is preferably larger in at least one dimension than the neck or opening of the aneurysm so that the closure structure substantially covers the neck of the aneurysm when deployed. The flexible patch may provide a substantially continuous surface or, in alternative embodiments, may have one or more openings to facilitate placement using a catheter system and/or to facilitate delivery of supplemental implantable devices or agents to the interior of the aneurysm following placement of the closure structure.

In another embodiment, the implantable device of the present invention comprises a closure structure having at least two flexible patches, each patch supported in proximity to its perimeter by a wire loop or framework structure. The device is delivered to the target site in a smaller dimension configuration and is deployed in the interior of an aneurysm such that one of the flexible patches substantially covers the neck of the aneurysm and another flexible patch contacts a wall of the aneurysm to stabilize the device within the aneurysm and to bias the flexible patch covering the neck of the aneurysm in position against the neck of the aneurysm. In this embodiment, the implantable device is located substantially entirely within the interior of an aneurysm following deployment.

In another embodiment, the implantable device comprises a closure structure, substantially as described above, in combination with one or more anchoring structure(s). An anchoring structure comprises at least two positioning loops mounted or otherwise associated with the closure structure. The positioning loops, in a deployed condition, are configured and sized to contact interior walls of the aneurysm and/or blood vessel walls in proximity to the aneurysm and to bias the closure structure against the wall of the aneurysm or against blood vessel walls in proximity to the neck of the aneurysm, thereby retaining the closure structure in place substantially covering the neck of the aneurysm.

In a deployed condition, the closure structure and the anchoring structure(s) may be positioned either inside or outside the neck of the aneurysm. In one embodiment, for example, the implantable device is deployed in the interior of an aneurysm such that opposed anchoring structures contact the interior wall of the aneurysm and the closure structure substantially covers the entrance or neck of the aneurysm, with the perimeter of the closure structure in the interior of the aneurysm or contacting the vessel wall in proximity to the neck of the aneurysm. In another embodiment, the implantable device is deployed in the blood vessel at the aneurysm such that anchoring structures contact the wall of the blood vessel, with the perimeter of the closure structure substantially covering the neck of the aneurysm and contacting the blood vessel wall in proximity to the neck of the aneurysm. Depending on the configuration of the anchoring structure(s), multiple anchoring loops may be positioned on the vessel wall in proximity to and/or generally opposite the neck of the aneurysm following deployment.

In yet another embodiment, the implantable device comprises a closure structure having a substantially tapered or truncated conical portion joined to a closure membrane and an anchoring structure comprising at least two positioning members. In this embodiment, the tapered portion of the closure structure preferably comprises a discontinuous mesh structure constructed from a shape change metallic material that, during deployment, expands to contact at least a portion of the internal wall of the aneurysm. The base of the tapered, discontinuous mesh structure is preferably joined to or associated with a closure membrane that, in a deployed condition, substantially covers the neck of the aneurysm. Anchoring structures are associated with the closure structure and may comprise a plurality of positioning loops that, in a deployed condition, contact at least a portion of a vessel wall in proximity to the neck of the aneurysm. According to another embodiment, the anchoring structures comprise at least two petal-like structures comprising, for example, metallic structures associated with permeable or impermeable coverings. According to yet another embodiment, the anchoring structure may comprise a second tapered, discontinuous mesh structure having a shallower configuration than that of the closure structure.

The flexible patche(es) comprising closure structures of the present invention are generally constructed from a flexible material or membrane mounted to a support structure that can be delivered through a catheter and, in a deployed condition, assumes a larger dimension configuration. In one embodiment, the flexible patch is constructed from a material that is substantially impermeable to liquids such as blood and bodily fluids. Alternatively, the flexible patch may be constructed from a material that is semi-permeable to liquids such as blood and bodily fluids and allows some exchange across the membrane. The membrane may comprise, for example, a medical grade silicone material, a fabric material such as Dacron, a fluropolymer composition such as a polytetrafluoroethylene (PTFE) material such as Goretex or Teflon, or the like, that is biocompatible and biostable and compressible, foldable or otherwise deformable for assuming a low diametric profile in a delivery condition for loading into or mounting to a delivery catheter. The membrane may comprise multiple layers, and it may have a variety of coatings or other materials associated with it, such as adherent or bonding substances, therapeutic substances, radioopaque markers, and the like.

The membrane may have a substantially continuous surface area or it may be provided with one or more openings or slots facilitating placement of the implantable device or mounting of the device on a catheter or delivery system in a delivery condition. The membrane is secured to a metallic loop or framework structure preferably comprising a shape change material by forming, bonding, suturing, or the like.

The framework supporting the closure structure and the anchoring structures are preferably constructed from a biocompatible shape change material that exhibits super-elastic behavior and/or shape memory properties, such as shape memory alloys. The shape change material changes shape in a predictable manner upon application of a shape change force such as heat, current or the like, to assume its predetermined, deployed condition. The force for producing the shape change is generally a change in temperature produced, for example, by introducing the device into a body temperature environment, by applying heat to the device using an external heating mechanism, or by heating the device by applying current through a conductive element. Upon heating of the shape memory material to, or above, a phase transition temperature of the material, the device framework structure and/or anchoring structure(s) assume their predetermined, larger dimension configuration.

Nitinol alloys exhibiting super-elastic behavior and shape memory properties are preferred shape memory alloys for use in devices of the present invention. The closure structure framework and anchoring loops may be formed, for example, from solid wire, tubular wire, braided materials, or the like. The closure structure framework and anchoring loops may have numerous configurations, depending on the device application, and may be generally circular, elliptical, oval, polygonal or the like. In some embodiments, closure structure elements and/or anchoring elements may have a mesh-like configuration.

The closure structure is generally delivered to a target site using a delivery catheter or a specialized microcatheter (referred to collectively as a "delivery catheter") or using a pusher system with a detachment mechanism. In one system, for example, the closure structure is detachably mounted to the distal end of a delivery catheter in a low profile condition and is covered and retained in the low profile condition by a retractable sheath. The delivery catheter may be positioned at or within the neck of an aneurysm using conventional techniques and, upon retraction of the sheath, the closure structure assumes its predetermined, deployed condition and is placed across the neck of the aneurysm.

In this embodiment, the closure structure placed across the neck of the aneurysm may have a central opening or slot mounted on the delivery catheter for delivery in the low profile condition and through which the delivery catheter may be withdrawn. According to methods of the present invention using this system, additional embolic devices such as coils, liquid or particulate embolics, or the like, may be introduced through a delivery catheter inserted through an opening of the closure structure. The additional embolic devices may act to bias the perimeter of the closure device against the interior wall of the aneurysm and thereby assist in retaining the closure structure in position substantially covering the neck of the aneurysm.

Implantable devices of the present invention may alternatively be delivered to the target site through a delivery catheter using a pusher system and detachment mechanism. The closure structure and supporting framework and positioning structures are generally radially compressed along the delivery axis in a delivery condition. In embodiments that utilize a pusher system and detachment mechanism, implantable devices incorporate a detachment element that is released during deployment. Detachment mechanisms known in the art, including mechanical, electrolytic, hydraulic and other systems may be utilized for deployment of implantable devices of the present invention.

In one deployment system, a device wire is mounted on or associated with an implantable device of the present invention. A proximal end of the device wire is mountable or mounted in proximity to a detachment mechanism comprising a shape change activation element having a generally linear configuration and being fixedly connected at its proximal end to a delivery wire, conduit, catheter or the like. The proximal end of the device wire and the distal end of the activation element have mating attachment mechanisms that, in a delivery condition, provide reliable attachment and guidance of the implantable device to the desired detachment site. Detachment of the activation element from the device wire following placement of the device at a desired location is accomplished by applying a shape change force, such as heat or current, to the activation element, producing a shape change in the activation element that releases the device wire, allowing withdrawal of the activation element and delivery wire.

BRIEF DESCRIPTION OF THE DRAWINGS

Various aspects of applicants' claimed inventions are illustrated schematically in the accompanying drawings, which are intended for illustrative purposes only and are not drawn to scale.

FIG. 1A illustrates a closure structure having a flexible patch supported by a framework structure. FIG. 1B shows the closure structure mounted on a delivery catheter in a delivery condition underneath a retractable sheath. FIG. 1C illustrates placement of the delivery catheter in proximity to the neck of the aneurysm for deployment of the closure structure, with the aneurysm partially broken away to show placement of the delivery catheter. FIG. 1D illustrates deployment of the closure device to substantially cover the aneurysm neck, with the aneurysm partially broken away to show placement of the deployed device. FIG. 1E illustrates the aneurysm target site following deployment of the closure device and delivery of embolic devices to the internal space of the aneurysm, with the aneurysm partially broken away to show placement of the deployed device and embolic devices.

FIG. 2 illustrates an enlarged schematic view of another implantable closure device of the present invention having two flexible patches in a deployed condition in an aneurysm, with the aneurysm and blood vessel shown in cross-section.

FIG. 3 illustrates an enlarged schematic front perspective view of another implantable closure device of the present invention in a deployed condition.

FIGS. 7A-7C illustrate the implantable closure device of FIGS. 6A and 6B in partially and fully deployed conditions.

FIG. 7A shows the implantable closure device being inserted into the neck of an aneurysm; FIG. 7B shows the device of FIG. 6B in dashed lines a deployed condition inside an aneurysm and blood vessel; and FIG. 7C shows the device of FIG. 6B in a deployed condition inside an aneurysm with the aneurysm and blood vessel shown in cross-section.

DETAILED DESCRIPTION OF THE INVENTION

Implantable devices and methods of the present invention are described and illustrated, in detail, with respect to their application as aneurysm closure devices. It will be appreciated that these devices and methods are not limited to this application and may be adapted and utilized in connection with the treatment of other vessel or air passageway cavities, abnormalities, or the like.

Figure 1A:
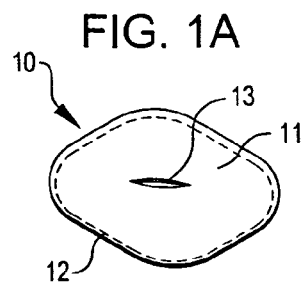
FIGS. 1A-1E show enlarged schematic views illustrating an implantable closure device of the present invention and deployment of the closure device at a target aneurysm site.

FIG. 1A-1E illustrate an implantable device of the present invention. FIG. 1A shows a closure structure 10 comprising a flexible patch 11 mounted or retained on a framework structure 12 and optionally having an opening or slot 13 provided in a generally central portion of patch 11. In one embodiment, patch 11 comprises a biocompatible and biostable material that is substantially impermeable to solids and liquids, such as a medical grade silicone material, a fluoropolymer material such as a PTFE composition such as Gore-Tex or Teflon, a woven or non-woven fabric material such as Dacron, or the like. Patch 11 may be provided as a single layer or membrane or may comprise multiple layers of the same or different materials. Patch 11 may also be coated or impregnated or otherwise associated with materials such as bonding agents, therapeutic substances, embolic substances, or the like.

The framework structure 12 may be in the form of a loop or strut-like framework structure having a perimeter structure generally corresponding to the configuration of the patch perimeter and preferably secured to the patch, at least in proximity to the perimeter of the patch. The framework structure may additionally support patch 11 at locations other than in proximity to its perimeter. Framework structure 12 preferably comprises a biocompatible and biostable shape change material, such as a shape memory alloy, such as a Nitinol™ alloy. Patch 11 may be secured to framework structure 12 by means such as bonding of the patch to itself or to the framework structure, suturing, or the like.

Closure structure 10 may have any of a variety of configurations such as generally round, oval, oblong or polygonal, for example. The size and perimeter configuration of closure structure 10 is designed to be at least slightly larger, in at least one dimension, than the neck or opening of an aneurysm desired to be closed. In a deployed condition, closure structure 10 preferably covers substantially the entire opening of an aneurysm.

Figure 1B:
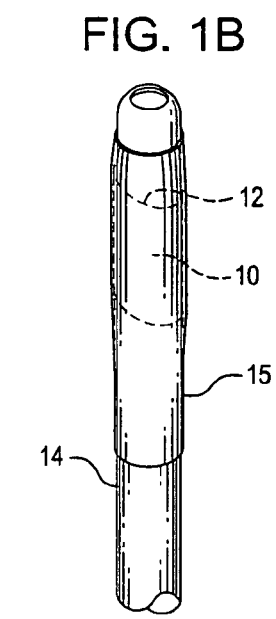
Figure 1C:
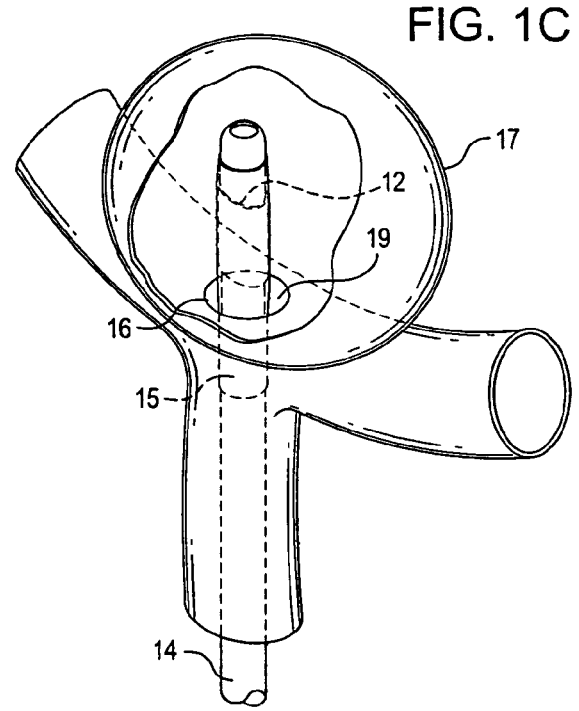
Figure 1D:
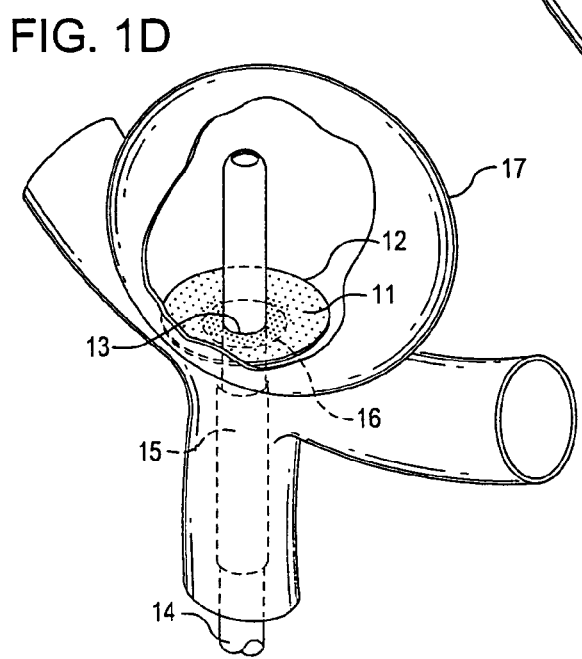
Figure 1E:
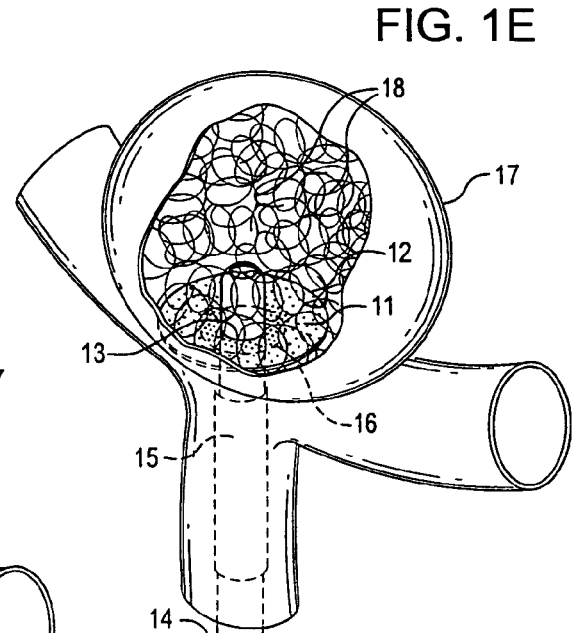

FIG. 1B schematically illustrates a delivery system in which closure structure 10 is mounted in close association with an outer surface of a delivery catheter 14 and retained underneath a retractable sheath 15 in a delivery condition. In this embodiment, closure structure 10 presents a low profile and closely conforms to the configuration of delivery catheter 14. During delivery and placement of closure structure 10, delivery catheter 14 is navigated through a subject's vasculature and positioned through an opening 19 of the neck 16 of a bulge of aneurysm 17, as illustrated in FIG. 1C. When sheath 15 is retracted, closure device 10 is restored to its predetermined deployed condition, as illustrated in FIG. 1D. In the deployed condition, framework structure 12 is in a larger dimension configuration and supports patch 11. In the deployed condition, portions of patch 11 and/or framework structure 12 preferably contact inner surfaces of the neck 16 of the aneurysm. Delivery catheter 14 may be withdrawn or additional embolic materials or substances, such as embolic coils 18 may be introduced through delivery catheter 14 to the interior of aneurysm 17, as illustrated in FIG. 1E. Embolic coils 18 are used in accordance with a conventional treatment regimen and additionally bias a perimeter portion of patch 11 against an inner surface of the neck 16 of aneurysm 17, thereby retaining patch 11 in place across the aneurysm opening and reducing or preventing the exchange of materials between the blood vessel and the aneurysm interior.

Although the closure structure illustrated in FIGS. 1A-1E is illustrated in connection with a deployment system in which the patch and framework structure are coaxially arranged on or in association with a delivery catheter and deployed upon retraction of a sheath, alternative device deployment devices and detachment systems of the present invention may be used to navigate closure structure 10 to a target site and deploy it at the target site. In alternative embodiments, closure structure 10 may comprise a device wire mounted at a generally central portion of the closure structure.

FIG. 2 schematically illustrates another embodiment of a closure device 20 of the present invention in a deployed condition inside an aneurysm 25. Closure device 20 comprises at least two patches 21 and 22 supported by a framework structure 23. Patches 21 and 22 are similar in structure and configuration to patch 11, described above, and patches 21 and 22 may have the same or different sizes and/or configurations and may be constructed from the same or different materials. In a preferred embodiment, at least two patches 21 and 22 are generally opposed to one another in a deployed condition. If more than two patches are provided, the patches are generally provided in a radially symmetrical configuration.

Framework structure 23 may be provided as an integral structure that includes framework elements supporting patches 21 and 22 in proximity to their perimeters and additionally comprises framework elements connecting patches 21 and 22, or separate but interconnected framework elements may be used. Closure device 20 may be coaxially arranged on or in association with a delivery catheter and deployed upon retraction of a sheath, as described above with reference to closure device 10. Alternatively, closure device 20 may be used with a detachment system and comprise a device wire of the type described in detail below mounted at a generally central portion of the closure structure. Following deployment, one of the patches 22 is positioned across the neck of the aneurysm 25 and the other patch 21 is positioned against the wall of the aneurysm, supporting the wall and biasing patch 22 in position across the neck of the aneurysm.

FIG. 3 illustrates another embodiment of a closure device 30 of the present invention comprising a patch 31 mounted to or associated with two anchoring structures 32, 33. The properties and configuration of patch 31 are generally as described with reference to patch 11, above. Patch 31 is supported by a framework structure 34 provided at least in a perimeter portion of patch 31 and attached to patch 31 by means of bonding, suturing, or the like. Framework structure 34 is mounted to or associated with wing-like anchoring structures 32, 33 and both framework structure 34 and anchoring structures preferably comprise a shape change material such as a Nitinol™ alloy material.

Anchoring structures 32, 33 may comprise a solid wire or tubular structure, or may be formed from a material having a braided construction or another mesh-like structure. The configuration of anchoring structures 32, 33 in a deployed condition is designed so that at least a portion of anchoring structures 32, 33 contact an inner wall of an aneurysm or an inner wall of an associated blood vessel following deployment. The configuration of anchoring structures 32, 33 may be generally circular, oblong, or otherwise form a curvilinear configuration, or they may form a polygonal configuration. In a preferred embodiment, as illustrated in FIG. 3, anchoring structures 32, 33, are generally oblong curvilinear structures that curve outwardly from attachment joint 35 to framework structure 34 and then back inwardly toward one another at the end remote from attachment joint 35. In the embodiment illustrated in FIG. 3, anchoring loops 32, 33 are form generally the same configuration and are generally the same dimension. In another embodiment, the anchoring structures may have different configurations and/or dimensions. In one embodiment, for example, one of the anchoring structures may be longer and/or wider than the other anchoring structure, or the anchoring structures may have different three-dimensional curvilinear or polygonal configurations. Although two anchoring structures 32, 33 are illustrated, it will be appreciated that additional anchoring structures may be provided. Anchoring structures are preferably arranged in a generally symmetrical fashion with respect to framework structure 34 and/or patch 31.

Figure 4:
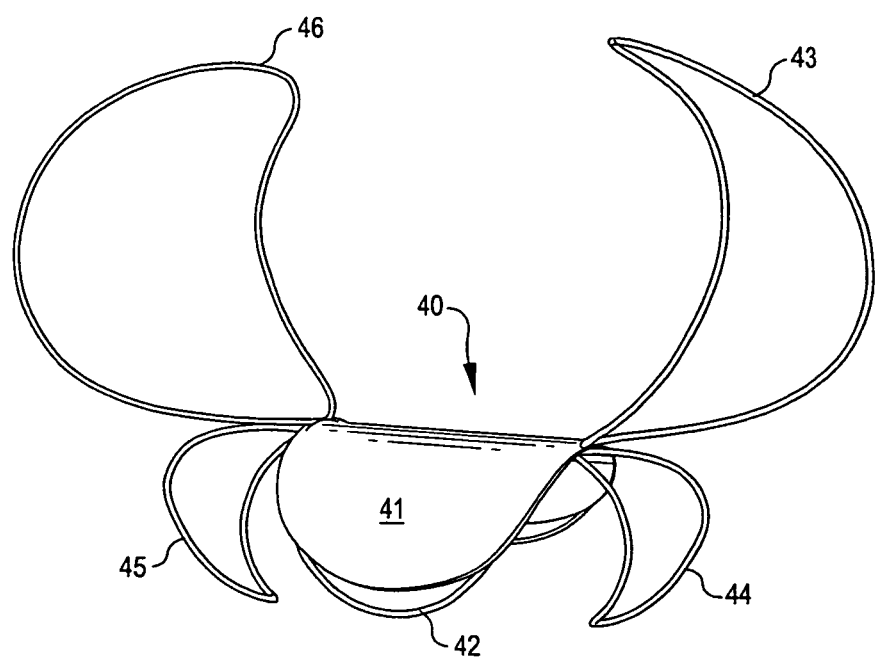
FIG. 4 illustrates an enlarged schematic end perspective view of another implantable closure device of the present invention in a deployed condition.

FIG. 4 illustrates another closure device 40 of the present invention comprising a patch 41 supported by a framework structure 42 and mounted to or associated with anchoring structures 43, 44, 45 and 46. The properties and configuration of patch 41 are generally as described with reference to patch 11, above. Patch 41 is supported by a framework structure 42 provided at least in a perimeter portion of patch 41 and attached to patch 41 by means of bonding, suturing, or the like. Framework structure 42 is mounted to or associated with two pairs of wing-like anchoring structures 43, 44 and 45, 46. Framework structure 42 and anchoring structures 43, 44, 45 and 46 preferably comprise a shape change material such as a Nitinol™ alloy material and may comprise a solid wire or tubular structure, or may be formed from a material having a braided construction or another mesh-like structure.

The configuration of anchoring structures 43, 44, 45 and 46, in a deployed condition, is designed so that at least a portion of each of anchoring structures 43, 44, 45 and 46 contacts an inner wall of an aneurysm or an inner wall of an associated blood vessel following deployment. The configuration of anchoring structures 43, 44, 45 and 46, in a deployed condition, may be generally circular, oblong, or otherwise form a curvilinear configuration, or they may form a polygonal configuration. In a preferred embodiment, as illustrated in FIG. 5, anchoring structures 43, 44, 45 and 46 are generally oblong curvilinear structures that curve outwardly from an attachment joint to framework structure 42 and then back inwardly toward one another at the end remote from framework structure 42. In the embodiment illustrated in FIG. 5, anchoring loops 43, 44, 45 and 46 form generally the same configuration and are generally the same dimension. Anchoring loops 43 and 46 are positioned in a generally mirror image orientation with respect to anchoring loops 44 and 45, respectively. Similarly, 43 and 44 are positioned in a generally mirror image orientation with respect to anchoring loops 46 and 45, respectively. In alternative embodiments, the configuration and/or dimension of each of anchoring loops 43, 44, 45 and 46 may vary and properties of patch 11, and having an anchoring structure comprising multiple positioning members 53, 54, 55 and 56.

Tapered closure structure 51 preferably comprises a discontinuous mesh structure constructed from a shape change metallic material that in a delivery condition provides a low profile, small diameter structure and expands during deployment to an enlarged, deployed condition in which it contacts a least a portion of the internal wall of the aneurysm. The mesh-like structure may have generally large or small spaces between the structures and the spaces and structures may be symmetrical or asymmetrical and may be generally curved or generally linear and angular. Suitable types of expanding mesh-like structures are known and used, for example, in various types of stents. Tapered closure structure 51 may be covered or associated, at least in part, with a flexible fabric or membrane material that is biocompatible and biostable such as a silicone material, a PFTE material, Dacron, or the like, or may be associated with other types of fibrous materials.

Tapered closure structure 51 may be joined to or associated with closure membrane 52 at a smaller diameter base portion 57. Closure structure 51 may have a perimeter that corresponds generally to the configuration of smaller diameter base portion 57 or, alternatively, the perimeter of closure structure 51 may have a larger or differently shaped configuration from that of smaller diameter base portion 57. In one embodiment, for example, closure structure 51 is mounted on or associated with a framework structure 58 in proximity to its perimeter and is mounted to or associated with base portion 57 at a location internal to its perimeter.

Positioning members 53, 54, 55 and 56 of closure device 50 may have a loop-like structure similar to the anchoring structures described above. Alternatively, positioning members 53, 54, 55 and 56 may comprise a solid metallic structure, a mesh-like discontinuous structure, or a structure in which a flexible material is mounted on or associated with framework structures defining the positioning members. Two or more positioning members may be provided and are arranged in a generally radially symmetrical arrangement with respect to closure structure 51. In another embodiment, a tapered, discontinuous mesh structure having a shallower configuration than that of tapered closure structure 51 may be provided as an anchoring structure.

FIGS. 7A-7C illustrate the closure device 50 in a deployed condition following deployment in and across an aneurysm. FIG. 7A illustrates closure device 50 partially inserted into an aneurysm A. Following deployment, tapered closure structure 51 is the configuration and/or dimension of each of anchoring loops 43, 44, 45 and 46 may be different. Although two pairs of generally opposed anchoring structures are illustrated, it will be appreciated that additional anchoring structures or pairs of opposed anchoring structures may be provided. Anchoring structures are preferably arranged in a generally symmetrical fashion with respect to framework structure 42 and/or patch 41.

Figure 5A:
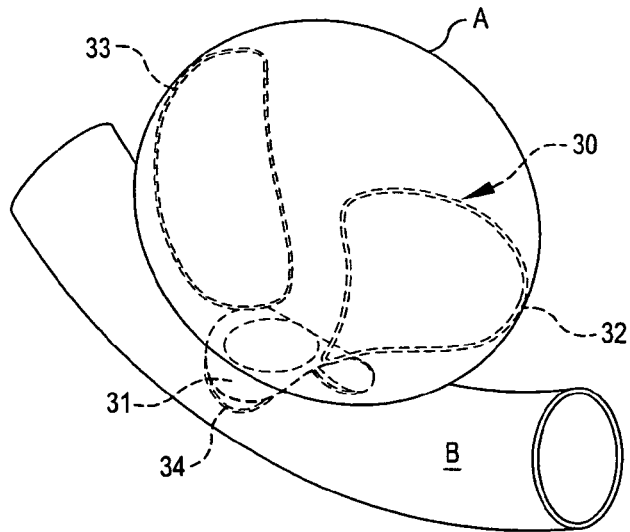
FIGS. 5A-5E schematically illustrate the implantable closure devices of FIGS. 3 and 4 deployed at a vessel irregularity.
Figure 5B:
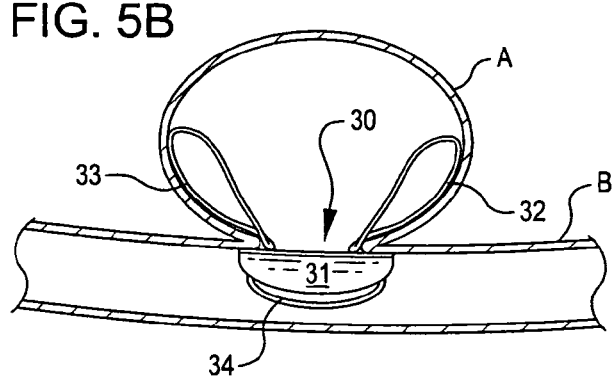
Figure 5C:
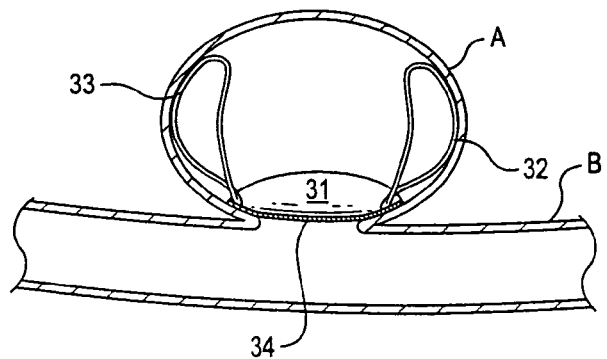

FIGS. 5A-5E schematically illustrate the closure devices of FIGS. 3 and 4 deployed at the site of an aneurysm. A bulge in blood vessel B forms an aneurysm A. As shown in FIGS. 5A and 5B, in one embodiment, when closure device 30 is deployed across the neck of and within aneurysm A, patch 31 is positioned to cover the opening of the aneurysm and anchoring structures 32 and 33 are retained inside and contact an inner aneurysm wall along at least a portion of their surface area. In this fashion, patch 31 and framework portion 34 are supported across the aneurysm opening and biased against the neck of the aneurysm from outside the aneurysm. In the embodiment illustrated in FIGS. 5A and 5B, patch 31 and framework portion 34 are deployed outside the internal space of the aneurysm. In an alternative embodiment illustrated in FIG. 5C, patch 31 and framework portion 34 are supported across the aneurysm opening and biased against the neck of the aneurysm from inside the aneurysm.

Figure 5D:
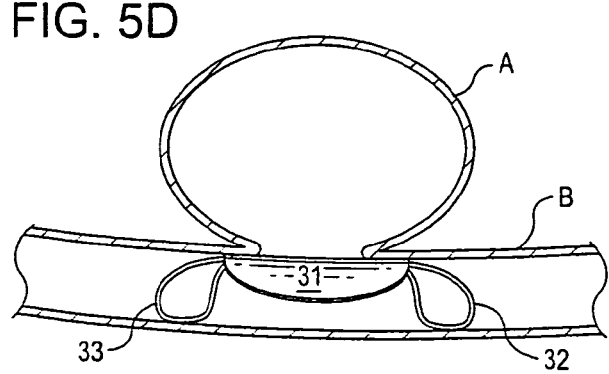
Figure 5E:
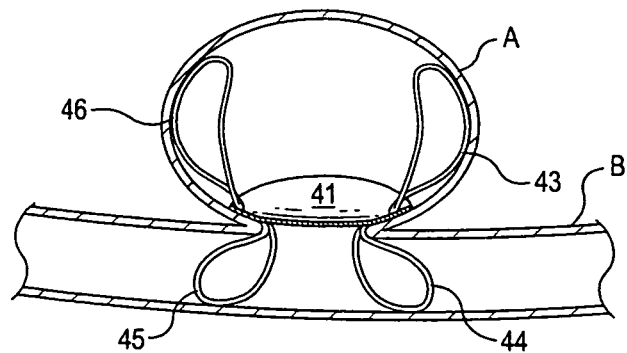

FIG. 5D illustrates an alternative deployment system and methodology, wherein a closure device having at least two anchoring structures is deployed such that patch 31 is positioned to cover the opening of the aneurysm and the anchoring structures 32, 33 are positioned outside the aneurysm and contact an inner blood vessel wall in proximity to the aneurysm. In general, using this methodology, the anchoring structures contact portions of the blood vessel wall at a location generally opposite the neck of the aneurysm. In yet another deployment system and methodology illustrated in FIG. 5E, a closure device of the type shown in FIG. 4 is deployed such that patch 41 is positioned to cover the opening of the aneurysm, with two of the anchoring structures positioned inside the aneurysm, contacting at least a portion of the aneurysm wall, and two of the anchoring structures positioned outside the aneurysm, contacting an inner blood vessel wall in proximity to the aneurysm.

Figure 6A:
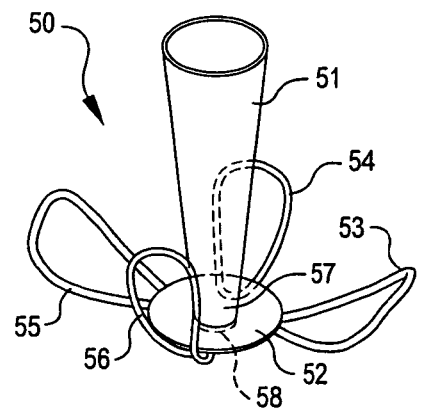
FIGS. 6A and 6B illustrate enlarged, schematic front perspective views of another implantable closure device of the present invention, with the device of FIG. 6A in a partially deployed condition and the device of FIG. 6B in a fully deployed condition.
Figure 6B:
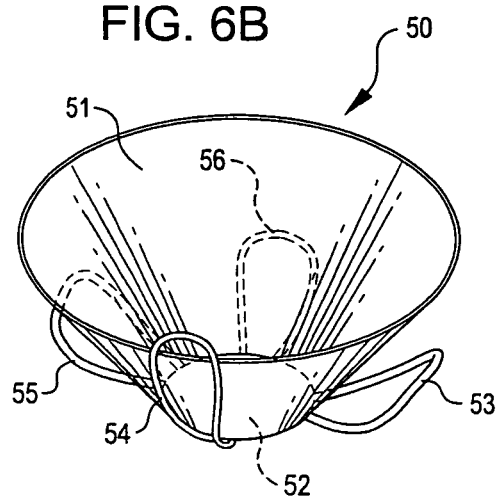

Alternative embodiments of aneurysm closure devices of the present invention are illustrated in a partially deployed condition in FIG. 6A and a fully deployed condition in FIG. 6B. In this embodiment, closure device 50 comprises a tapered closure structure 51 having a generally truncated conical configuration joined to a closure membrane 52 having the positioned within the aneurysm and membrane 52 extends across and substantially closes the opening of the aneurysm. The anchoring structure, composed of at least two positioning members or a tapered, mesh structure, and illustrated in FIGS. 7B and 7C as positioning members 53, 54, 55 and 56, resides outside the aneurysm following deployment and contacts at least a portion of the blood vessel wall in proximity to the neck of the aneurysm.

In another aspect, the implantable systems of the present invention comprise a closure device, as disclosed in detail above, having a device wire that, in combination with a detachment joint, detachably connects the implantable device wire to a delivery/pusher wire. A device wire is generally integral with or attached at its distal end to the implantable device through the detachment joint and employed to deliver the implantable device to the desired location in the body, generally by navigation through a guide catheter. Suitable device wires, detachment joints and delivery/pusher wires are well known in the art and may be used in association with closure devices of the present invention. Other materials that may be employed for the device and delivery wires are well known in the art.

While in the foregoing specification this invention has been described in relation to certain preferred embodiments thereof, and many details have been set forth for purposes of illustration, it will be apparent to those skilled in the art that the invention is susceptible to various changes and modification as well as additional embodiments and that certain of the details described herein may be varied considerably without departing from the basic spirit and scope of the invention.

All of the patent references and publications cited in this specification are incorporated by reference herein in their entireties.

We claim:

1. An implantable aneurysm closure device adjustable from a delivery arrangement in which the device has a generally small diameter configuration to a deployed arrangement in which the device has a larger diameter configuration, the implantable aneurysm closure device comprising:
    a tapered closure structure having a generally truncated conical configuration, wherein the closure structure comprises an open distal end and is configured to contact at least a portion of an internal wall of an aneurysm when the device is in the deployed arrangement;
    a closure membrane having a first major surface and a second major surface opposite the first surface, wherein the first surface is coupled with a base of the tapered closure structure, and wherein the closure membrane is sized to substantially cover an opening of the aneurysm when the device is in the deployed arrangement; and
    an anchoring structure comprising at least two positioning members extending away from the closure membrane and biased toward the tapered closure structure, and wherein, in the deployed arrangement, the at least two positioning members are configured to reside outside the aneurysm and extend generally beyond a periphery of the closure membrane.

2. The implantable aneurysm closure device of claim 1 wherein the tapered closure structure comprises a discontinuous mesh structure constructed from a shape change material.

3. The implantable aneurysm closure device of claim 1 wherein the tapered closure structure is covered, at least in part, with a flexible membrane material.

4. The implantable aneurysm closure device of claim 1 wherein the tapered closure structure is associated with the closure membrane at a smaller diameter base portion, and wherein the closure membrane extends beyond the smaller diameter base portion of the tapered closure structure.

5. The implantable aneurysm closure device of claim 1 wherein a larger perimeter end of the tapered closure structure opposite the base portion including an opening having a diameter larger than that of the base portion.

6. The implantable aneurysm closure device of claim 1 wherein the tapered closure structure is configured to contact only a proximal portion of the internal wall of the aneurysm when the device is in the deployed arrangement.

7. The implantable aneurysm closure device of claim 1 wherein the at least two positioning members, in the deployed arrangement, are configured to be biased toward an inner wall of a blood vessel in proximity to the aneurysm.

8. The implantable aneurysm closure device of claim 1 wherein the at least two positioning members comprise wire loops.

9. The implantable aneurysm closure device of claim 1 wherein the closure structure comprises a substantially continuous occlusive surface area.

10. The implantable aneurysm closure device of claim 1 wherein the closure structure is composed of a material that is substantially impermeable to fluids.

11. The implantable aneurysm closure device of claim 1 wherein the closure structure is composed of a material that is semi-permeable or permeable to fluids and allows at least limited exchange of fluids across the structure.

12. The implantable aneurysm closure device of claim 1 wherein the at least two positioning members comprise a first positioning member and a second positioning member having at least approximately identical configurations.

13. The implantable aneurysm closure device of claim 1 wherein the at least two positioning members comprise a first positioning member and a second positioning member having different configurations.

14. The implantable aneurysm closure device of claim 1 wherein the at least two positioning members comprise a first positioning member extending in a first direction from the closure membrane, and a second positioning member extending in a second, opposite direction from the closure membrane.

15. The implantable aneurysm closure device of claim 1 wherein the at least two positioning members are composed of a biocompatible shape memory alloy material.

16. The implantable aneurysm closure device of claim 1 wherein the closure membrane comprises a generally cylindrical structure extending in a plane generally orthogonal to that of the tapered closure structure in the deployed arrangement.

17. The implantable aneurysm closure device of claim 1 wherein the at least two positioning members are discrete, independent components coupled to the second surface of the closure membrane.

* * * * *

UNITED STATES PATENT AND TRADEMARK OFFICE
CERTIFICATE OF CORRECTION

PATENT NO. : 8,545,530 B2  
APPLICATION NO. : 11/324827  
DATED : October 1, 2013  
INVENTOR(S) : Joseph Eskridge et al.

It is certified that error appears in the above-identified patent and that said Letters Patent is hereby corrected as shown below:

On the title page, item (56), References Cited, in column 2, under "Other Publications", line 1, delete "Concourse" and insert -- Concours --, therefor.

On title page 3, item (56), References Cited, in column 1, under "Other Publications", line 1, delete "Microcather," and insert -- Microcatheter, --, therefor.

On title page 3, item (56), References Cited, in column 2, under "Other Publications", line 15, delete "Polytetraflouroethylene" and insert -- Polytetrafluoroethylene --, therefor.

In the Specification

Column 1, line 64, delete "injectible" and insert -- injectable --, therefor.

Column 6, line 59, delete "fluropolymer" and insert -- fluoropolymer --, therefor.

Column 6, line 67, delete "radioopaque" and insert -- radiopaque --, therefor.

Signed and Sealed this  
Second Day of December, 2014

Michelle K. Lee  
*Deputy Director of the United States Patent and Trademark Office*